US011491126B2

(12) United States Patent
Clements

(10) Patent No.: US 11,491,126 B2
(45) Date of Patent: *Nov. 8, 2022

(54) METHOD FOR REDUCING LUNG INFLAMMATION

(71) Applicant: Respirion Pharmaceuticals Pty Ltd, Iluka (AU)

(72) Inventor: Barry Clements, Iluka (AU)

(73) Assignee: Respirion Pharmaceuticals PTY LTD, Iluka (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/615,075

(22) PCT Filed: Jun. 20, 2018

(86) PCT No.: PCT/AU2018/050609
§ 371 (c)(1),
(2) Date: Nov. 19, 2019

(87) PCT Pub. No.: WO2018/232452
PCT Pub. Date: Dec. 27, 2018

(65) Prior Publication Data
US 2020/0163920 A1 May 28, 2020

(30) Foreign Application Priority Data

Jun. 20, 2017 (AU) .............................. 2017902365

(51) Int. Cl.
*A61K 9/00* (2006.01)
*A61P 11/00* (2006.01)
*A61P 29/00* (2006.01)
*A61K 31/198* (2006.01)

(52) U.S. Cl.
CPC .......... *A61K 31/198* (2013.01); *A61K 9/0078* (2013.01); *A61P 11/00* (2018.01); *A61P 29/00* (2018.01)

(58) Field of Classification Search
CPC ...... A61K 9/0078; A61K 9/00; A61K 47/183; A61K 31/198; A61P 11/00; A61P 29/00
See application file for complete search history.

(56) References Cited

U.S. PATENT DOCUMENTS 5,823,178 A 10/1998 Lloyd et al.
2016/0263151 A1 9/2016 Hassett

FOREIGN PATENT DOCUMENTS

WO WO-2008/137747 11/2008
WO WO-2017/096013 6/2017

OTHER PUBLICATIONS

Asmus et al., Pulmonary function response to EDTA, an additive in nebulized bronchodilators, 107(1):68-72, Jan. 2001.
Beasley et al., Bronchoconstrictor Properties of Preservatives in Ipratropium Bromide (Atrovent) Nebuliser Solution, 294(6581):1197-8, May 1987.
Brown et al., Edetate Sodium Aerosol in Pseudomonas Lung Infection in Cystic Fibrosis, American Journal of Diseases of Children, 139(8):836-9, Aug. 1985.
Gaggar et al., The role of matrix metalloproteinases in cystic fibrosis lung disease, European Respiratory Journal, 38(3):721-727, Sep. 2011.
Garratt et al., Matrix metalloproteinase Activation by Free Neutrophil Elastase Contributes to Bronchiectasis Progression in Early Cystic Fibrosis, The European Respiratory Journal, 46(2):384-94, Aug. 2015.
Hunter et al., Ferrous Iron is a Significant Component of Bioavailable Iron in Cystic Fibrosis Airways, mBio, 4(4):1-8, Aug. 2013.
Hassett et al., A Putative ABC Transporter Permease is Necessary for Resistance to Acidified Nitrite and EDTA in Pseudomonas aeruginosa under Aerobic and Anaerobic Planktonic and Biofilm Conditions, Front Microbiology, 7:291, Apr. 2016.
Jomova et al., Advances in Metal-Induced Oxidative Stress and Human Disease, Toxicology, 283(2-3):65-87, May 2011.
Kettle et al., Oxidation contributes to low glutathione in the airways of children with cystic fibrosis, European Respiratory Journal, 44(1):122-9, Jul. 2014.
Macnee, W., Oxidative Stress and Lung Inflammation in Airways Disease, European Journal of Pharmacology, 429(1-3):195-207, Oct. 2001.
Schultz et al., Airway surface liquid pH is not acidic in children with cystic fibrosis, Nature Communications, 8(1):1409, Nov. 2017.
Sly et al., Lung disease at diagnosis in infants with cystic fibrosis detected in newborn screening, American Journal of Respiratory and Critical Care Medicine, 180(2):146-52, Jul. 2009.
Stites et al., Increased Concentrations of Iron and Isoferritins in the Lower Respiratory Tract of Patients with Stable Cystic Fibrosis, 160(3):796-80, Nov. 1998.
Hillman, K., Twigley, A., Aerosol EDTA to eliminate respiratory-tract pseudomonas, Lancet, 2(8394):99, Jul. 1984.
Aoki et al., Efficacy of Calcium-EDTA as an Inhibitor for Metallo-β-Lactamase in a Mouse Model for Pseudomonas aeruginosa Pneumonia, Antimicrobial Agents and Chemotherapy, 54(11):4582-4588, Nov. 2010.
Zarogiannis et al., Ascorbate and Deferoxamine Administration after Chlorine Exposure Decrease Morality and Lung Injury in Mice, American Journal of Respiratory Cell and Molecular Biology, 45(2):386-392, Aug. 2011.
Petrovic et al., Aerosol Inhalation of CaNa2E.D.T.A (MOSATIL) by Workers Constantly Exposed to Lead Poisoning, British Journal of Industrial Medicine, 17(3):201-204, Jul. 1960.
Kumar et al., Edetate calcium disodium nanoparticle dry powder inhalation: a novel approach against heavy metal decorporation, International Journal of Pharmaceutics, 416(1):376-383, Sep. 2011.
International Search Report and Written Opinion issued on International Patent Application No. PCT/AU2018/050609, dated Jul. 16, 2018.
International Preliminary Report on Patentability issued on International Patent Application No. PCT/AU2018/050609, dated Dec. 24, 2019.

(Continued)

*Primary Examiner* — Sun Jae Yoo
(74) *Attorney, Agent, or Firm* — Colleen M. Schaller; Howson & Howson LLP

(57) ABSTRACT

A method of treating or preventing inflammation in the lung by administering a high concentration of an inhaled chelating agent.

6 Claims, 6 Drawing Sheets

(56) References Cited

OTHER PUBLICATIONS

Clarkson, A. B. Jr. et al. "Action of deferoxamine against Pneumocystis carinii" Antimicrobial Agents and Chemotherapy, Dec. 2001. vol. 45, No. 12, p. 3560-3565. doi:10.1128/AAC.45.12.3560-3565.
Aali, M. et al. "Iron chelation as novel treatment for lung inflammation in cystic fibrosis" Medical Hypotheses. May 2017, vol. 104. p. 86-88. doi:10.1016/j.mehy.2017.05.029.

$*= p<0.05$ $*= p<0.05$

METHOD FOR REDUCING LUNG INFLAMMATION

CROSS-REFERENCE TO RELATED APPLICATIONS

This is a National Stage Entry under 35 U.S.C. 371 of International Patent Application No. PCT/AU2018/050609, filed Jun. 20, 2018, which claims priority to Australian Patent Application No. 2017902365, filed Jun. 20, 2017. These applications are incorporated by reference herein.

TECHNICAL FIELD

The present invention relates to a method of treating or preventing inflammation in the lung by administering a high concentration of an inhaled chelating agent, and formulations to use in the method. In one embodiment of the invention, the inflammation in the lung is associated with or caused by cystic fibrosis.

BACKGROUND ART

Cystic fibrosis is characterised by susceptibility to infection, which contributes to inflammation and lung damage. However, inflammation and lung damage may also occur in the absence of bacterial infection (Sly et al. *Am J Respir Grit Care Med.* 2009 180(2):146-52).

Inflammation is the body's response to insults, which include infection, trauma, and hypersensitivity. The inflammatory response is complex and involves a variety of mechanisms to defend against pathogens and repair tissue. In the lung, inflammation is usually caused by pathogens or by exposure to toxins, pollutants, irritants, and allergens.

During inflammation, numerous types of inflammatory cells are activated. Each releases cytokines and mediators to modify activities of other inflammatory cells. Orchestration of these cells and molecules leads to progression of inflammation. Clinically, acute inflammation is seen in diseases such as pneumonia and acute respiratory distress syndrome (ARDS), whereas chronic inflammation is represented by diseases such as asthma, cystic fibrosis and chronic obstructive pulmonary disease (COPD). Because the lung is a vital organ for gas exchange, excessive inflammation can be life threatening. A delicate balance between inflammation and anti-inflammation is essential for lung homeostasis.

Immunity involves innate and adaptive systems. Innate immunity is nonspecific and evokes rapid responses, including inflammation in face of pathogen insults. Adaptive immunity is antigen-specific. It first detects the specific antigen and then mobilizes inflammatory cells to target that particular antigen. The innate and adaptive systems share components and act in concert to defend against pathogens.

The airway epithelium secretes a variety of substances such as mucins, defensins, lysozyme, lactoferrin, and nitric oxide, which non-specifically shield the respiratory tract from microbial attack. The epithelial cells also produce a number of mediators such as reactive oxygen radicals, cytokines (TNF-α, IL-1β, granulocyte/macrophage colony-stimulating factor [GM-CSF]), and platelet-activating factor to recruit inflammatory cells onto the site of inflammation. The cytokines stimulate arachidonic acid release from membrane lipids, leading to production of eiconasoids, which further stimulate mucus secretion by goblet cells and tissue inflammation.

Surfactant lies on the surface of alveoli and contains four surfactant proteins (SP A-D). Important for reducing lung surface tension, these proteins play a critical role in surfactant absorption into the alveolar surface. SP-A and SP-D also participate in host defence. They bind bacterial surface molecules, modulate leukocyte activity, and lead to pathogen opsonization.

IgA secreted by plasma cells forms an additional epithelial protective barrier, which prevents microbial adherence to the epithelial surface. It also binds to pathogens, causing phagocytosis and antibody-dependent cell-mediated cytotoxicity. Immunoglobulin E (IgE) induces immediate type hypersensitivity in the respiratory tract. It produces severe reactions by binding to IgE receptors on the surfaces of mast cells, basophils, eosinophils, and B lymphocytes. Repeat exposure to the same antigen induces degranulation and the release of pro-inflammatory mediators, including histamine, prostaglandins, leukotrienes, and tryptase. These increase vascular permeability, bronchoconstriction, and inflammatory cell infiltration.

US20160263151 teaches the use of an inhaled antibiotic, in combination with acidified nitrite and an iron chelator, to treat bacterial infections. The iron chelator present in the formulations of US20160263151 serves to provide a synergistic effect when combined with the acidified nitrite, enhancing the ability of the antibiotic to act.

Current treatments for lung inflammation include oral or inhaled steroids and non-steroidal medications that target the host inflammatory responses. However, the effects are transient, require continuous treatment and there are significant side effects.

There is a need for methods to treat or prevent inflammation in the lung; or at least a method for complimenting or providing an alternative to the previously known treatment methods.

The present invention seeks to provide an improved or alternative method for treating or preventing inflammation in the lung, by administering a high concentration of an inhaled chelating agent.

The preceding discussion of the background art is intended to facilitate an understanding of the present invention only. The discussion is not an acknowledgement or admission that any of the material referred to is or was part of the common general knowledge as at the priority date of the application.

SUMMARY OF INVENTION

The present invention provides a method of treating or preventing inflammation in the lung by administering a high concentration of an inhaled chelating agent.

Preferably, the high concentration of an inhaled chelating agent is greater than 37.5 mg/dose.

Preferably, the high concentration of an inhaled chelating agent is greater than 50 mg/dose.

In one form of the invention, the high concentration chelating agent is provided by a dosage form containing at least 50 mg/dose, or between 50 mg/dose and 300 mg/dose. The chelating agent may be administered between one and four times daily, up to a total dose of about 1,200 mg/day, preferably at least 150 mg/day.

In one form of the invention, the high concentration chelating agent is provided in a dosage form containing at least 37.5 mg/dose or between 37.5 mg/dose and 300 mg/dose. The chelating agent may be administered between one and four times daily, up to a total dose of up to about 1,200 mg/day, preferably at least 150 mg/day.

Preferably from 37.5 mg/day to 1,200 mg/day of chelating agent is administered. Preferably, at least 50 mg/day of chelating agent is administered. The chelating agent may be administered between one and four times daily, up to a total daily dose of about 1,200 mg/day.

Preferably, each dose of the chelating agent is administered over a period of no more than is administered over a period of no more than 8 hours. Preferably, the chelating agent and/or antibiotic are administered over a period of no more than 1 h.

Preferably the chelating agent is CaEDTA.

The present invention further provides a method of treating or preventing inflammation in the lung by administering a high concentration of an inhaled chelating agent wherein the treatment or prevention of inflammation results in an increase in forced expiratory volume (FEV).

The present invention also provides a method of treating or preventing inflammation in the lung by administering a high concentration of an inhaled chelating agent wherein the treatment or prevention of inflammation is associated with a decrease in matrix metalloproteinase (MMP) activity.

The present invention further provides a method of treating or preventing inflammation in the lung by administering a high concentration of an inhaled chelating agent wherein the treatment or prevention of inflammation is associated with a decrease in the production of hydroxyl radicals.

The present invention provides an inhalable formulation containing a high concentration of a chelating agent.

The present invention provides an inhalable formulation containing a high concentration of a chelating agent and capable of delivering a high concentration of an inhalable chelating agent as a single dose.

The present invention provides a kit for treating or preventing inflammation in the lung containing (i) an inhalable formulation containing a high concentration of a chelating agent; and (ii) instructions for use.

The present invention provides a kit for treating or preventing inflammation in the lung containing (i) an inhalable formulation capable of delivering a high concentration of an inhalable chelating agent as a single dose; and (ii) instructions for use.

The use of a high concentration of a chelating agent in the manufacture of an inhalable formulation for treating or preventing inflammation in the lung.

The use of an inhalable chelating agent in the manufacture of a medicament for the delivery of a high concentration of the inhalable chelating agent as a single dose for treating or preventing inflammation in the lung.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIG. 5 shows total leukocyte count in bronchoalveolar lavage fluid (BALF) from mice exposed to air or cigarette smoke (CS) and treated by intranasal administration of either vehicle or deferoxamine (DFO). While cigarette smoke induces the number of leukocytes as expected, treatment with DFO significantly reduces this effect.

FIG. 6 shows lung weight of mice exposed to air or CS and treated with vehicle or DFO as above. Lung weight can be used as a surrogate for inflammation with increased weight indicating more inflammation. In CS-treated mice, lung weight is significantly increased as expected, and DFO treatment reduces the mean weight, suggesting reduced inflammation.

FIG. 7 shows that while CS increases the BALF iron content, treatment with deferoxamine reduces this effect. Left: Average iron content for each group of mice; Right: Scatter plot of the same data.

DESCRIPTION OF INVENTION

Detailed Description of the Invention

Method of Treatment or Prevention

Figure 1A:
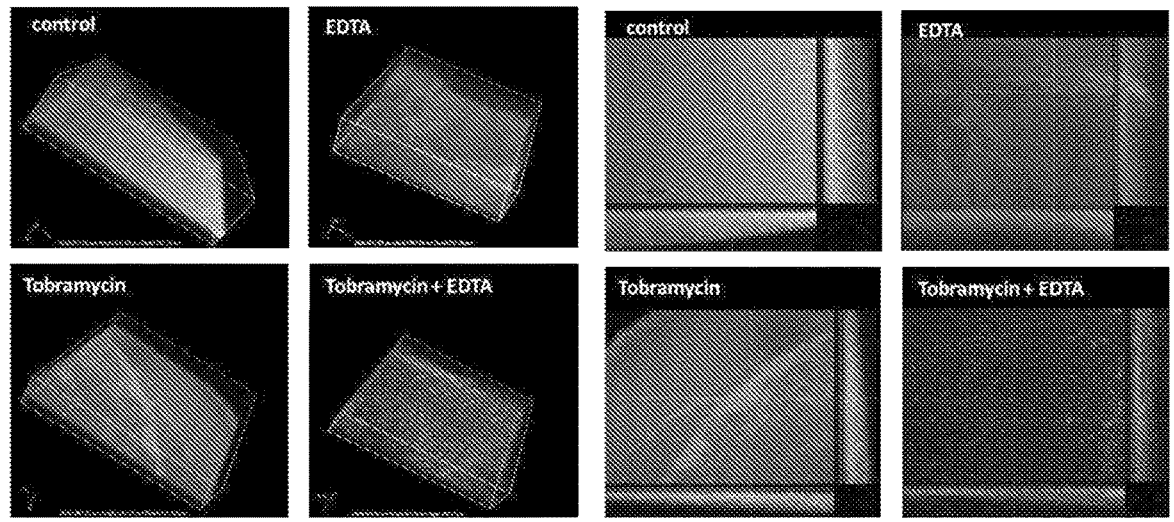
FIG. 1 shows submicron particles of EDTA kill *P. aeruginosa* biofilms and act synergistically with tobramycin in vitro. *P. aeruginosa* biofilms in CF mucus, treated with aerosolised EDTA particles and/or tobramycin. The final concentration of tobramycin in the droplets was 325 µg/ml. 1A) Confocal microscopy images of biofilms stained with BacLight LIVE/DEAD. 1B) Bacterial counts showing the quantitative effect of treatments.

The present invention provides a method of treating or preventing inflammation in the lung by administering a high concentration of an inhaled chelating agent.

Preferably, the high concentration of an inhaled chelating agent is greater than 37.5 mg/dose.

Preferably, the high concentration of an inhaled chelating agent is greater than 50 mg/dose.

It has previously been shown that inhaled EDTA alone does not treat bacterial infections (Brown et al. (*Am J Dis Child*. 1985 139(8):836-9); Hassett (*Front Microbiol*. 2016 7:291)). Brown et al. (1985) treated ten CF children chronically infected with *P. aeruginosa* with nebulised sodium EDTA for three months and observed no change in lung function. Others have reported that EDTA causes concentration-dependent bronchoconstriction (Beasley et al. (*Br Med J (Clin Res Ed)*. 1987 294(6581):1197-8)); and that EDTA has no effect on FEV1 (Asmus et al. (*J Allergy Clin Immunol*. 2001 107(1):68-72)). Therefore, there would be no reason to believe that a chelating agent would have any positive effect on subjects such as those with cystic fibrosis (CF), asthma, chronic obstructive pulmonary disease (COPD) or other conditions of the lung that cause or are associated with inflammation. However, the present invention has surprisingly found that inhaled chelating agent can treat or prevent lung inflammation.

It is a commonly held belief that the CF lung environment is acidic. However, it has been recently shown that the CF lung has the same pH as normal lungs (Schultz et al. "Airway surface liquid pH in children with cystic fibrosis". *Nature Communications* 2017 8(1):1409). Existing technology using acidified nitrite, such as that discussed in US20160263151, is therefore unlikely to work clinically in CF as the formulation does not remain acidified but immediately returns to the normal lung pH of 7.4.

While the acidity of the CF lung is normal, iron levels have been found to be strikingly different from normal lungs. Stites et al. (*Am J Respir Crit Care Med.* 1999 160(3):796-80) showed that iron levels are greatly elevated in the lungs of CF patients, as well as in the lungs of smokers, compared to healthy individuals. It has also been shown that most of this iron is in the ferrous form, Fe(II), and significantly correlates with disease severity (Hunter et al., MBio. 2013 4(4):1-8). Ferrous iron can participate in the Fenton reaction to generate highly reactive oxygen radicals that can severely damage tissues and DNA (Jomova et al. *Toxicology.* 2011 283(2-3):65-87; MacNee, *Eur J Pharmacol.* 2001 429(1-3):195-207).

Without wishing to be bound by theory, it is believed that the method of the present invention reduces inflammation by (i) inactivation of matrix metalloproteinases (MMPs) by the chelation of zinc; (ii) reducing the production of reactive oxygen species (ROS) by the chelation of iron; and/or (iii) reducing the bacterial load in the lungs by depriving the bacteria of essential ions such as iron and zinc. The action in an individual's lung may be a one or any combination of the theorised methods of reducing inflammation.

Inhalation is a localized administration method and can therefore be more effective in reaching the target area, i.e., the lung, and providing a high and localized concentration of the inhaled chelating agent. Inhalation avoids undesired side effects due to systemic exposure of the actives and reduces the risk of patients developing resistance.

The present invention further provides a method of treating or preventing inflammation in the lung by administering a high concentration of an inhaled chelating agent wherein the treatment or prevention of inflammation results in an increase in FEV.

The present invention further provides a method of treating or preventing inflammation in the lung by administering a high concentration of an inhaled chelating agent wherein the treatment or prevention of inflammation is associated with a decrease in MMP activity. It is known that matrix metalloproteinases (MMPs) cause lung damage (Garratt et al. *Eur Respir J.* 2015 46(2):384-94) and that MMP activity is $Zn^{2+}$ dependent (Hazra et al. *Molecular Vision* 2012; 18:1701-1711). However, previous attempts to target MMPs in lungs have been unsuccessful. The present invention uses an inhaled chelating agent to chelate zinc in the lungs, thus reducing MMP induced lung damage and treating or preventing inflammation.

The present invention further provides a method of treating or preventing inflammation in the lung by administering a high concentration of an inhaled chelating agent wherein the treatment or prevention of inflammation is associated with a decrease in the production of hydroxyl radicals. Iron is a key factor in lung damage (Stites et al. (*Am J Respir Crit Care Med.* 1999 160(3):796-80) as Fe catalyses the formation of hydroxyl radicals. However, antioxidant trials have so far failed to produce significant improvement in lung function. The present invention uses an inhaled chelating agent to chelate iron in the lungs, thus reducing hydroxyl radical induced lung damage and treating or preventing inflammation.

The present invention further provides a method of treating or preventing infection in the lung by administering a high concentration of an inhaled chelating agent wherein the treatment or prevention of inflammation results from the removal or reduction of bacterially produced biofilm in the lungs by the presence of the chelating agent. The reduction in biofilm allows increased removal of the bacteria and biofilm by coughing and expectoration.

The present invention further provides a method of treating or preventing inflammation in the lung by administering a high concentration of an inhaled chelating agent wherein the treatment or prevention of inflammation results from the removal or reduction of bacterially-produced protease enzymes, which can stimulate local inflammation, cause local tissue damage, and can neutralise antibiotic activity. These enzymes are largely cation dependant and removal of cations from the environment is expected to de-activate these enzymes.

Preferably, the chelating agent is an iron chelating agent or a zinc chelating agent. More preferably, the chelating agent is a chelator of both iron and zinc (an iron/zinc chelator). Alternatively, the chelating agent may be a mixture of two or more chelating agents, for example a mixture of an iron chelating agent and a zinc chelating agent, or an iron/zinc chelating agent and a zinc chelating agent, or an iron chelating agent and an iron/zinc chelating agent.

The chelating agent is preferably selected from the group consisting of citric acid, phosphates, the di-, tri- and tetra-sodium salts of ethylene diamine tetraacetic acid (EDTA), the calcium salts of EDTA, ethylene glycol-bis-(b-amino-ethylether)-N,N,N',N'-tetraacetic acid (EGTA); 1,2-bis(2-aminophenoxy)ethane-N,N,N',N'-tetraacetic acid (BAPTA); ethylene-N,N'-diglycine (EDDA); 2,2'-(ethylendiimino)-dibutyric acid (EBDA); lauroyl EDTA; dilauroyl EDTA, triethylene tetramine dihydrochioride (TRIEN), diethylenetriamin-pentaacetic acid (DPTA), triethylenetetramine hexaacetic acid (TTG), deferoxamine (DFO), deferasirox (DSX), dimercaprol, zinc citrate, penicilamine succimer, editronate, sodium hexmetaphosphate, edetate calcium disodium, D-penicillamine, polyphenols, gallol, catechol, dimercaprol, tetrathiomolybdate, lactoferrin, and clioquinol and combinations thereof.

Preferably, the chelating agent is a pharmaceutically acceptable chelating agent.

In one embodiment, the chelating agent is ethylene diamine tetraacetic acid (EDTA). In another embodiment, the chelating agent is deferoxamine (DFO). In another embodiment, the chelating agent is deferasirox (DSX).

Preferably, the chelating agent has approximately the same iron affinity as EDTA, and/or approximately the same zinc affinity as EDTA. The formation constant or stability constant (log $K_1$) for EDTA at 25° C. and 0.1 M is 14.3 for $Fe^{2+}$, 25.1 for $Fe^{3+}$ and 16.5 for zinc.

In one embodiment, the chelating agent is a calcium salt of the chelating agent. Preferably, the chelating agent is CaEDTA.

In one embodiment, the chelating agent is provided in an inhaled dose form containing between 37.5 mg/dose and 300 mg/dose, 50 mg/dose and 300 mg/dose, between about 75 mg/dose and 200 mg/dose, between about 75 mg/dose and 100 mg/dose, between about 37.5 mg/dose and 200 mg/dose, between about 50 mg/dose and 200 mg/dose; preferably about 37.5 mg/dose, 50 mg/dose, 75 mg/dose, 100 mg/dose, 200 mg/dose or 300 mg/dose. The chelating agent is preferably provided in an inhaled dose form containing at least 37.5 mg/dose. The chelating agent is preferably provided in an inhaled dose form containing at least 50 mg/dose.

The total amount of chelating agent inhaled per day is preferably between about 37.5 mg/day and 1,200 mg/day 50 mg/day and 1,200 mg/day, between about 100 mg/day and 1,000 mg/day, between about 300 mg/day and 900 mg/day, between about 400 mg/day and 800 mg/day; preferably about 150 mg/day, 300 mg/day, 500 mg/day or 600 mg/day.

The total amount of agent inhaled per day is preferably between about 0.1 mg chelating agent/kg body weight and 15 mg chelating agent/kg body weight, between about 0.5 mg chelating agent/kg body weight and 10 mg chelating agent/kg body weight, between about 1.0 mg chelating agent/kg body weight and 5 mg chelating agent/kg body weight; between about 1.0 mg chelating agent/kg body weight and 3.5 mg chelating agent/kg body weight; preferably about 1.0 mg chelating agent/kg body weight, 1.5 mg chelating agent/kg body weight, 2.0 mg chelating agent/kg body weight, 2.5 mg chelating agent/kg body weight, 3.0 mg chelating agent/kg body weight, 3.5 mg chelating agent/kg body weight, 4.0 mg chelating agent/kg body weight, 4.5 mg chelating agent/kg body weight, 5.0 mg chelating agent/kg body weight, 10 mg chelating agent/kg body weight, 15 mg chelating agent/kg body weight.

It has been determined that, if 75 mg of a chelating agent such as CaEDTA is inhaled, then about 0.4 mM to 1.34 mM chelating agent may be detected in the sputum from the lungs after 5 min.

The inhaled chelating agent is preferably delivered over a period of no more than 8 h, 7 h, 6 h, 5 h, 4 h, 3 h, 2 h, 1 h, 45 min, 30 min, 20 min, 15 min, 10 min, or 5 min. If the administration is by dry powder delivery, then the inhaled chelating agent may be delivered over a period of seconds, for example 1 second per "puff" of aerosol device or dry powder inhaler, wherein one or more puffs are administered at each time point.

Preferably the inhaled chelating agent is administered for at least 28 consecutive days. The inhaled chelating agent may be delivered for 2 days or more, 3 days, 4 days, 5 days, 6 days or 7 days. The inhaled chelating agent may be delivered for between 2 and 28 days, 1 week, 2 weeks, 3 weeks or 4 weeks.

Some subjects may benefit from a period of "loading" the subject with antibiotic and/or the chelating agent, with a higher dose or more frequent administration over a period of days or weeks, followed by a reduced or maintenance dose.

Thus the present invention:

- delivers a total amount of inhaled chelating agent of between 37.5 mg/day and 1,200 mg/day;
- is administered at least once per day up to six times per day, preferably up to four times a day;
- is administered over a period of no more than 8 h.

Preferably, the present invention:

- delivers a total amount of inhaled chelating agent of between 37.5 mg/day and 1,200 mg/day;
- is administered once or twice per day;
- is administered over a period of no more than 1 h per administration;
- contains CaEDTA as the chelating agent.

The preferable amount of any chelating agent may be calculated by comparing the chelating capacity of the agent to that of CaEDTA, and then multiplying the dosage range given above by that number. The result should provide a level of chelation approximately equal to the preferred level of chelation provided by the preferred amount of EDTA.

Preferably, the inflammation is caused by, causes or is associated with the following lung conditions: cystic fibrosis (CF); asthma; chronic obstructive pulmonary disease (COPD); pulmonary hypertension; lung cancer; pulmonary fibrosis; bronchiectasis; bronchitis; bronchiolitis; acute respiratory distress syndrome; tuberculosis; nontuberculous mycobacterial (NTM) pulmonary infections; pneumonia including but not limited to ventilator associated pneumonia, community acquired pneumonia, bronchial pneumonia, lobar pneumonia; infections by bacteria such as *Pseudomonas* spp, *Streptococcus pneumoniae, Chlamydia, Mycoplasma* pneumonia, *Staphylococci* spp, *Klebsiella* spp, *E. coli, Stenotrophomonas* spp, and fungi, including *Aspergillus, Scedosporium* and *Candida* sp; prophylactive treatment or prevention for conditions in which infection might arise e.g. intubated or ventilated patients; infections in lung transplant patients; bronchitis; pertussis (whooping cough); inner ear infections; streptococcal throat infections; inhalation anthrax; tularemia; or sinusitis.

Preferably, the formulation is administered to the subject in need between about once per day to about 6 times per day, more preferably about 4 times per day.

Alternatively, the formulation may be administered to the subject in need via continuous inhalation, via a nebuliser. The nebulised formulation may be delivered for 24 hours, 12 hours, 8 hours, 6 hours, 4 hours, 2 hours or 1 hour, and each of these deliveries (apart from the 24 and 12 hour) may be repeated several times within a 24 hour period.

A subject will typically receive a dose of about 0.01 to 15 mg/kg/day of a chelating agent, ±20% or ±10%. This dose will typically be administered either nebulised or by at least one, preferably several "puffs" from the aerosol device. For example, a subject may receive between 0.1 mg/kg chelating agent and 15 mg/kg in a single dose, or in several doses over a day.

The total dose per day is preferably administered at least once per day, but may be divided into two or more doses per day. Some subjects may benefit from a period of "loading" the subject with the chelating agent with a higher dose or more frequent administration over a period of days or weeks, followed by a reduced or maintenance dose. As cystic fibrosis, COPD etc., are typically chronic conditions, subjects are expected to receive such therapy over a prolonged period of time.

Regardless of the form of the drug formulation, it is preferable to create droplets or particles for inhalation in the range of about 0.1 μm to 12 μm, or about 0.25 μm to 6 μm, preferably 1 μm to 6 μm, and more preferably about 2 μm to 4 μm. Alternatively, the particles may be 0.1 μm to 1.0 μm, 0.2 μm to 0.9 μm, 0.3 μm to 0.8 μm, 0.4 μm to 0.7 μm, or 0.5 μm. By creating inhaled particles which have a relatively narrow range of size, it is possible to further increase the efficiency of the drug delivery system and improve the repeatability of the dosing. Thus, it is preferable that the particles not only have a size in the range of 0.1 μm to 12 μm or 2 μm to 6 μm or about 3 to 4 μm but that the mean particle size be within a narrow range so that 80% or more of the particles being delivered to a subject have a particle diameter which is within ±20% of the average particle size, preferably ±10% and more preferably ±5% of the average particle size.

"Particle size" is a notion introduced for comparing dimensions of solid particles, liquid particles (droplets). For droplets and aerosols, terms such as "aerodynamic diameter" and "mass median aerodynamic diameter (MMAD) are used. The definitions are given below.

"Aerodynamic diameter" is the diameter of a unit-density sphere having the same terminal settling velocity as the particle in question. It is used to predict where in the respiratory tract such particles will deposit.

"Mass Median Aerodynamic Diameter" is the geometric mean aerodynamic diameter. Fifty percent of the particles by weight will be smaller than the MMAD, 50% will be larger.

During particle sizing experiment, the suspensions contain innumerable number of particles of varying sizes in motion. When the particle-sizing machine analyzes these particles, it forms a particle distribution curve, which covers the entire particle size range starting from the smallest particle, which could be 1 nm to the largest, which could be 100 μm. In the particle size distribution curve, a cumulative frequency is calculated for the particles. $D_{10}$ refers to that particular particle diameter where 10% of the particles in the suspension have a smaller diameter or equal diameter as that of the particular particle diameter.

$D_{50}$: Similar to the $D_{10}$, $D_{50}$ is the cut off diameter for 50% of the particle population in the formulation and refers to that particular particle diameter where 50% of the particles in the suspension have a smaller diameter or equal diameter as that of the particular particle diameter.

$D_{90}$: $D_{90}$ is the cut off diameter for 90% of the particle population in the formulation and refers to that particular particle diameter where 90% of the particles in the suspension have a smaller diameter or equal diameter as that of the particular particle diameter.

The term "respiratory tract" shall be taken to mean a system of cells and organs functioning in respiration, in particular the organs, tissues and cells of the respiratory tract include, lungs, nose, nasal passage, paranasal sinuses, nasopharynx, larynx, trachea, bronchi, bronchioles, respiratory bronchioles, alveolar ducts, alveolar sacs, alveoli, pneumocytes (type 1 and type 2), ciliated mucosal epithelium, mucosal epithelium, squamous epithelial cells, mast cells, goblet cells, and intraepithelial dendritic cells.

In one form of the invention, the method of treating or preventing inflammation in the lung of a subject comprises administering a therapeutically effective or preventative effective concentration of an inhaled chelating agent, in the form of one or more doses of at least 37.5 mg/dose, wherein the or each dose of the chelating agent is administered over a period of no more than 8 h.

In one form of the invention, the method of treating inflammation in the lung of a subject comprises administering a therapeutically effective concentration of an inhaled chelating agent, in the form of one or more doses of at least 37.5 mg/dose, wherein the or each dose of the chelating agent is administered over a period of no more than 8 h.

In one form of the invention, the method of preventing inflammation in the lung of a subject by administering a preventative effective concentration of an in an inhaled chelating agent, in the form of one or more doses of at least 37.5 mg/dose, wherein the or each dose of the chelating agent is administered over a period of no more than 8 h.

In one form of the invention, the method of treating or preventing inflammation in the lung of a subject comprises treating or preventing inflammation in the lung of a subject in need of such treatment.

The term a "therapeutically effective amount" as used herein means an amount of the formulation, which when administered according to a desired dosage regimen, is sufficient to at least partially attain the desired therapeutic effect, or delay the onset of, or inhibit the progression of, halt, partially or fully the onset or progression of the inflammation.

The term a "preventative effective amount" as used herein means an amount of the formulation, which when administered according to a desired dosage regimen, is sufficient to at least partially prevent or delay the onset of the inflammation.

As used herein, "treating" or "treatment" refers to inhibiting the disease or condition, i.e., arresting or reducing its development or at least one clinical or subclinical symptom thereof. "Treating" or "treatment" further refers to relieving the disease or condition, i.e., causing regression of the disease or condition or at least one of its clinical or subclinical symptoms. The benefit to a subject to be treated is either statistically significant or at least perceptible to the subject and/or the physician. In the context of treating inflammation, the term treatment includes reducing or eliminating one or more of leukocyte infiltration (including macrophages, polymorphonuclear neutrophils, lymphocytes and other immune cells); immunoglobulins; pro-inflammatory cytokines and chemokines and their receptors; noxious mediators such as ROS and proteolytic enzymes; MMP abundance and activity; markers of oxidative stress; as well as bronchial hyperreactivity and exacerbations. The term treatment further includes one or more of an increase in anti-inflammatory cytokines, and an increase in lung function (FEV1).

Based on the above, it will be understood by those skilled in the art that a plurality of different treatments and means of administration can be used to treat a single subject. Thus, subjects already receiving such medications, for example, as intravenous ciprofloxacin or antibiotics, etc., may benefit from inhalation of the formulations of the present invention. Some subjects may receive only the present formulations of a high concentration of a chelating agent by inhalation. Such subjects may have symptoms of cystic fibrosis, be diagnosed as having lung infections, or have symptoms of a medical condition, which symptoms may benefit from administration to the subject of a high concentration of a chelating agent. The formulations of the invention may also be used diagnostically. In an embodiment, for example, a subject may receive a dose of a formulation of the invention as part of a procedure to diagnose lung infections, wherein one of more of the subject's symptoms improves in response to the formulation.

Dosage Form

The present invention provides an inhalable formulation containing a high concentration of a chelating agent.

The inhalable formulation may be in dry powder form for inhalation, or in nebulised form for inhalation. Preferably, the formulation is adapted for inhalation to treat or prevent inflammation in the lung.

In one embodiment, the chelating agent is a calcium salt of the chelating agent. Preferably, the chelating agent is CaEDTA.

Preferably, the high concentration of an inhaled chelating agent is greater than 37.5 mg/dose. Preferably, the high concentration of an inhaled chelating agent is greater than 50 mg/dose. Preferably the high concentration chelating agent is provided in a dosage form containing between 37.5 mg/dose and 300 mg/dose, between 50 mg/dose and 300 mg/dose, between about 75 mg/dose and 200 mg/dose, between about 75 mg/dose and 100 mg/dose, between about 50 mg/dose and 200 mg/dose; preferably about 50 mg/dose, 75 mg/dose, 100 mg/dose, 200 mg/dose or 300 mg/dose. The chelating agent is preferably provided in an inhaled dose form containing at least 37.5 mg/dose. The chelating agent is preferably provided in an inhaled dose form containing at least 50 mg/dose.

The total amount of chelating agent inhaled per day is preferably between about 37.5 mg/day and 1,200 mg/day, 50 mg/day and 1,200 mg/day, between about 100 mg/day and 1,000 mg/day, between about 300 mg/day and 900 mg/day, between about 400 mg/day and 800 mg/day; preferably about 300 mg/day, 500 mg/day or 600 mg/day. The chelating agent may be administered up to a total dose of up to about 1,200 mg/day, preferably at least 150 mg/day.

The total amount of chelating agent inhaled per day is preferably between about 37.5 mg/day and 1,200 mg/day, about 50 mg/day and 1,200 mg/day, between about 100 mg/day and 1,000 mg/day, between about 300 mg/day and 900 mg/day, between about 400 mg/day and 800 mg/day; preferably about 150 mg/day, 300 mg/day, 500 mg/day or 600 mg/day.

The total amount of chelating agent inhaled per day is preferably between about 0.1 mg chelating agent/kg body weight and 15 mg chelating agent/kg body weight, between about 0.5 mg chelating agent/kg body weight and 10 mg chelating agent/kg body weight, between about 1.0 mg chelating agent/kg body weight and 5 mg chelating agent/kg body weight; between about 1.0 mg chelating agent/kg body weight and 3.5 mg chelating agent/kg body weight; preferably about 1.0 mg chelating agent/kg body weight, 1.5 mg chelating agent/kg body weight, 2.0 mg chelating agent/kg body weight, 2.5 mg chelating agent/kg body weight, 3.0 mg chelating agent/kg body weight, 3.5 mg chelating agent/kg body weight, 4.0 mg chelating agent/kg body weight, 4.5 mg chelating agent/kg body weight, 5.0 mg chelating agent/kg body weight, 10 mg chelating agent/kg body weight, 15 mg chelating agent/kg body weight.

For example, a 50 mg dose of CaEDTA may be administered as 4 ml nebulised solution at 33 mM (molecular mass $C_{10}H_{12}CaN_2Na_2O_8$ is 274.27 g/mol). Similarly, a 75 mg dose may be administered in 4 ml at 50 mM, or a 100 mg dose may be administered in 4 ml at 66 mM.

Preferably, the formulation is administered to the subject in need between about once per day to about 6 times per day, more preferably about 4 times per day.

Alternatively, the formulation may be administered to the subject in need via continuous inhalation, via a nebuliser. The nebulised formulation may be delivered for 24 hours, 12 hours, preferably 8 hours, 6 hours, 4 hours, 2 hours or 1 hour, and each of these deliveries (apart from the 24 and 12 hour) may be repeated several times within a 24-hour period.

The formulations of the invention may be administered to a subject using a disposable package and portable, handheld, battery-powered device, such as the AERx device (U.S. Pat. No. 5,823,178, Aradigm, Hayward, Calif.). Alternatively, the formulations of the instant invention may be carried out using a mechanical (non-electronic) device. Other inhalation devices may be used to deliver the formulations including conventional jet nebulizers, ultrasonic nebulizers, soft mist inhalers, dry powder inhalers (DPIs), metered dose inhalers (MDIs), condensation aerosol generators, and other systems.

For use as aerosols, the compounds of the present invention in solution or suspension may be packaged in a pressurized aerosol container together with suitable propellants, for example, hydrocarbon propellants like propane, butane, or isobutane with conventional adjuvants. A dry powder inhaler is a system operable with a source of pressurized air to produce dry powder particles of a pharmaceutical formulation that is compacted into a very small volume. For inhalation, the system has a plurality of chambers or blisters each containing a single dose of the pharmaceutical formulation and a select element for releasing a single dose.

An aerosol may be created by forcing drug through pores of a membrane which pores have a size in the range of about 0.25 to 6 μm (U.S. Pat. No. 5,823,178). When the pores have this size the particles which escape through the pores to create the aerosol will have a diameter in the range of 0.5 to 12 μm. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency, pressure, and other parameters based on the density and viscosity of the formulation keeping in mind that an object of some embodiments is to provide aerosolized particles having a diameter in the range of about 0.5 to 12 μm.

Excipients

The above-exemplified forms of the formulations described herein can be manufactured by methods well known to one of skill in the art of formulation science. Additionally, the formulations described herein may include other optional excipients to aid in the manufacturing and/or administration of the formulations described herein. Non-limiting examples of such excipients are well known in the art and include flavourings, colorants, palatants, antioxidants, viscosity modifying, tonicity agents, drug carriers, sustained-release agents, comfort-enhancing agents, emulsifiers, solubilizing aids, lubricants, binding agents and other stabilizing agents to aid in the manufacturing and/or administration of the formulations.

Preferably, the present formulation is sterile. In another embodiment, the formulation of the present invention is stable.

Further, buffering agents may be added to adjust the pH level of the formulation. Preferably, the formulations of the present invention contain tris(hydroxymethyl)aminomethane (TRIS, also known as THAM or tromethamine) as a buffering agent. TRIS may have a further effect in increasing the effect of bacterial killing by EDTA. Preferably, TRIS is added to the formulations of present invention both to buffer the formulation and to increase the effectiveness of the EDTA and/or antibiotic in treating or preventing bacterial infections.

Moreover, the formulations of the present invention may contain an antimicrobial preservative.

Preferably, the pH of the formulations of the present invention is between about 6.5 and 8.0, more preferably about 7.0 and 7.4. It has previously been found that bacteria become more resistant to anti-microbial therapy the more the pH drops. The preferable pH assists in avoiding bacterial resistance to formulations containing a high concentration of an inhaled chelating agent in combination with an antibiotic in the absence of acidified nitrite.

In one alternate embodiment, the formulation of the present invention may comprise a preservative, suspending agent, wetting agent, tonicity agent and/or diluent. The formulations provided herein may comprise from about 0.01% to about 90%, or about 0.01% to about 50%, or about 0.01% to about 25%, or about 0.01% to about 10%, or about 0.01% to about 5% of one or more pharmacologically suitable suspending fluids which is physiologically acceptable upon administration by inhalation. Pharmacologically suitable fluids for use herein include, but are not limited to, polar solvents, including, but not limited to, compounds that contain hydroxyl groups or other polar groups. Solvents include, but are not limited to, water or alcohols, such as ethanol, isopropanol, and glycols including propylene glycol, polyethylene glycol, polypropylene glycol, glycol ether, glycerol and polyoxyethylene alcohols. Polar solvents also include protic solvents, including, but not limited to, water, aqueous saline solutions with one or more pharmaceutically acceptable salt(s), alcohols, glycols or a mixture there of. In one alternative embodiment, the water for use in the present formulations should meet or exceed the applicable regulatory requirements for use in inhaled drugs.

In one embodiment, the formulations described herein may be aqueous and contain 0-90% water. In other embodiments, the aqueous formulations described herein may contain 20-80% water. In still other embodiments, aqueous formulations may contain 50-70% water. The water may further comprise water that is plain, distilled, sterile, demineralized or deionized.

Alternatively, the formulation may be non-aqueous and contain no water, or negligible amounts of water (e.g. below 1%, below 0.1%, below 0.01%).

In one embodiment, the formulation further comprises one or more pharmaceutically or physiologically acceptable carriers, diluents or excipients.

In addition to or in lieu of sterilization, the formulations of the present invention may contain a pharmaceutically acceptable preservative to minimize the possibility of microbial contamination. Additionally, a pharmaceutically-acceptable preservative may be used in the present formulations to increase the stability of the formulations. It should be noted, however, that any preservative must be chosen for inhalation safety, as the treated tissues may be sensitive to irritants. Preservatives suitable for use herein include, but are not limited to, those that protect the solution from contamination with pathogenic particles, including phenylethyl alcohol, benzalkonium chloride or benzoic acid, or benzoates such as sodium benzoate and phenylethyl alcohol. In certain embodiments, the formulations herein comprise from about 0.001% to about 10.0% w/w of benzalkonium chloride, or from about 0.01% v/w phenylethyl alcohol. Preserving agents may also be present in an amount from about 0.001% to about 1%, preferably about 0.002% to about 0.02%, more preferably 0.02% w/w.

The formulations provided herein may also comprise from about 0.001% to about 90%, or about 0.001% to about 50%, or about 0.001% to about 25%, or about 0.001% to about 10%, or about 0.001% to about 1% of one or more emulsifying agent, wetting agent, or suspending agent. Such agents for use herein include, but are not limited to, polyoxyethylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan monooleate, polyoxyethylene (20) sorbitan monopalmitate, polyoxyethylene (20) sorbitan monostearate; lecithins; agar; carrageenan; locust bean gum; guar gum; tragacanth; acacia; xanthan gum; karaya gum; pectin; amidated pectin; ammonium phosphatides; microcrystalline cellulose; methylcellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyltartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-21 actylate; calcium stearoyl-2-lactylate; stearoyl tartrate; sorbitan monostearate; sorbitan tristearate; sorbitan monolaurate; sorbitan monooleate; sorbitan monopalmitate; extract of quillaia; polyglycerol esters of dimerised fatty acids of soya bean oil; oxidatively polymerised soya bean oil; and pectin extract.

The formulations of the present invention may comprise from about 0.001% to about 5% by weight of a humectant to inhibit drying of the mucous membrane and to prevent irritation. Any of a variety of pharmaceutically-acceptable humectants can be employed, including sorbitol, propylene glycol, polyethylene glycol, glycerol or mixtures thereof, for example.

The formulation of the present invention may further comprise an adjuvant, such as: a bronchodilator, another anti-inflammatory agent, a surfactant, aspirin, or ethyl alcohol.

Bronchodilators optionally used in the formulations of the invention include but are not limited to $\beta_2$-adrenergic receptor agonists (such as albuterol, bambuterol, salbutamol, salmeterol, formoterol, arformoterol, levosalbutamol, procaterol, indacaterol, carmoterol, milveterol, procaterol, terbutaline, and the like), and antimuscarinics (such as trospium, ipratropium, glycopyrronium, aclidinium, and the like). Combinations of drugs may be used.

Additional anti-inflammatories that may optionally be used in the formulations of the invention include but are not limited to inhaled corticosteroids (such as beclometasone, budesonide, ciclesonide, fluticasone, etiprednol, mometasone, and the like), leukotriene receptor antagonists and leukotriene synthesis inhibitors (such as montelukast, zileuton, ibudilast, zafirlukast, pranlukast, amelubant, tipelukast, and the like), cyclooxygenase inhibitors (such as ibuprofen, ketoprofen, ketorolac, indometacin, naproxen, zaltoprofen, lornoxicam, meloxicam, celecoxib, lumiracoxib, etoricoxib, piroxicam, ampiroxicam, cinnoxicam, diclofenac, felbinac, lornoxicam, mesalazine, triflusal, tinoridine, iguratimod, pamicogrel, and the like). Combinations of drugs may be used. Aspirin may also be added to act as an anti-inflammatory agent.

Surfactants covered by the invention include but are not limited to synthetic surfactant (Exosurf®), dipalmitoylphosphatidylcholine and oleic acid. Combinations of drugs may be used.

Antioxidants such as glutathione and vitamin E, zinc and zinc salts of EDTA, may be added.

Ethyl alcohol vapour acts as an anti-foaming agent in the lungs and makes sputum more liquid, which can aid breathing and reduce lung oedema. Ethanol may be added to the formulations of the present invention at between 0.5% and 60%, more preferably between 1 and 40%, 1 and 20%, or 1 and 10%. The ethanol may be added at 1%, 2%, 3%, 4%, 5%, 6%, 7%, 8%, 9%, 10%, 15%, 20%, 25%, 30%, 35%, 40%, 45%, 50%, 55% or 60%.

The invention also relates to the use of a high concentration of a chelating agent in combination with other drugs given via inhalation. These other drugs may include a nucleotide sequence which may be incorporated into a suitable delivery vector such as a plasmid or viral vector. The other drug may be a therapeutic nucleotide sequence (DNA, RNA, siRNA), enzymes to reduce the viscoelasticity of the mucus such as DNase and other mucolytic agents, chemicals to upregulate the chloride ion channel or increase flow of ions across the cells, nicotine, P2Y2 agonists, elastase inhibitors including $\alpha$-1 antitrypsin (AAT), N-acetylcysteine, antibiotics and cationic peptides, such as lantibiotics, and specifically duramycin, short-acting bronchodilators (e.g., $\beta$2-adrenergic receptor agonists like albuterol or indacaterol), M3 muscarinic antagonists (e.g., ipratropium bromide), K$^+$-channel openers, long-acting bronchodilators (e.g., formoterol, salmeterol), steroids (e.g., budesonide, fluticasone, triamcinolone, beclomethasone, ciclesonide, etc.), xanthines, leukotriene antagonists (e.g., montelukast sodium), phosphodiesterase 4 inhibitors, adenosine receptor antagonists, other miscellaneous anti-inflammatories (e.g., Syk kinase inhibitors (AVE-0950), tryptase inhibitors (AVE-8923 & AVE-5638), tachykinin antagonists (AVE-5883), inducible nitric oxide synthase inhibitors (GW-274150) and others), transcription factor decoys, TLR-9 agonists, antisense oligonucleotides, siRNA, DNA, CGRP, lidocaine, inverse β2-agonists, anti-infective oxidative therapies, cytokine modulators (e.g., CCR3 receptor antagonists (GSK-766994, DPC-168, AZD-3778), TNF-α production inhibitors (LMP-160 & YS-TH2), and IL-4 antagonists (AVE-0309)), small molecule inhibitors of IgE, cell adhesion molecule (CAM) inhibitors, small molecules targeting the VLA4 receptor or integrin .alpha.4.beta.1 (e.g., R-411, PS-460644, DW-908e, & CDP-323), immunomodulators including those that block T-cell signalling by inhibition of calcineurin (Tacrolimus), heparin neutralizers (Talactoferrin α), cytosolic PLA2 inhibitors (Efipladib), or combinations thereof. If the subject in need has CF, then they may also be administered standard medications such as ivacaftor, pulmozyme, mannitol, or other approved drugs according to standard practise, in combination with the formulations of the present invention.

The delivery of the combination products may be achieved by combining the drugs into one stable formulation, or providing the drugs in separate containers to be combined at the time of administration or alternatively by sequentially delivering the products.

Preferably, the formulations of the present invention are stable. As used herein, the stability of formulations provided herein refers to the length of time at a given temperature that greater than 80%, 85%, 90% or 95% of the initial amount of drug substance, e.g., chelating agent and antibiotic, is present in the formulation. For example, the formulations provided herein may be stored between about 15° C. and about 30° C., and remain stable for at least 1, 2, 12, 18, 24 or 36 months. Also, the formulations may be suitable for administration to a subject in need thereof after storage for more than 1, 2, 12, 18, 24 or 36 months at 25° C. Also, in another alternative embodiment, using Arrhenius Kinetics, more than 80%, or more than 85%, or more than 90%, or more than 95% of the initial amount of drug substance (e.g., chelating agent and antibiotic) remains after storage of the formulations for more than 1, 2, 12, 18, 24 or 36 months between about 15° C. and about 30° C.

As used herein, the statement that a formulation is stable during "long term storage" means that the formulation is suitable for administration to a subject in need thereof when it has an estimated shelf-life of greater than 1, 2 or 3 months usage time at 25° C. and greater than or equal to 1, 2 or 3 years storage time at 5° C. In certain embodiments herein, using Arrhenius kinetics, >80% or >85% or >90% or >95% estimated chelating agent and antibiotic remains after such storage.

The term "inflammation" as used herein means one or more signs of the body's response to insults, such infection, environmental assaults (including cigarette smoke), trauma or hypersensitivity. Inflammation can be either acute or chronic, and signs include swelling of tissues, recruitment of different types of inflammatory cells, release of cytokines and mediators, and bronchial hyperreactivity. Inflammation can be localised, subclinical or temporary, or it can be more widespread and may become chronic. Inflammation can include both humoral and cellular immune responses and may persist after the insult that triggered it has been removed. Signs of inflammation include, but are not limited to, elevated levels of inflammatory cells (e.g. dendritic cells, macrophages, neutrophils, lymphocytes, eosinophils and mast cells), elevated levels of pro-inflammatory cytokines (e.g. TNFα, IL-1β, IL-6, IL-8, and IFNγ) and their receptors, excessive proteases including MMPs, ROS and other mediators, and markers of inflammation such as C-reactive protein (CFP) and sputum and serum calprotectin. Inflammation in the short term ("acute"), will result in airway swelling, altered lung compliance, airway reactivity and mucus hypersecretion, with clinical symptoms which may include an increase in respiratory rate and difficulty, wheeze, cough, and a reduction in FEV1, and if it persists ("chronic"), will lead to airway wall and lung parenchymal structural damage in the form of fibrosis, cystic changes and bronchiectasis.

Methods of Manufacturing a Medicament

The use of a high concentration of a chelating agent in the manufacture of an inhalable formulation for treating or preventing inflammation in the lung.

The use of an inhalable chelating agent in the manufacture of a medicament for the delivery of a high concentration of the inhalable chelating agent as a single dose for treating or preventing inflammation in the lung.

Preferably the high concentration chelating agent is provided in a dosage form containing at least 37.5 mg/dose, at least 50 mg/dose, or between 50 mg/dose and 300 mg/dose, or between 37.5 mg/dose and 300 mg/dose. The chelating agent may be administered between one and four times daily, up to a total dose of up to about 1,200 mg/day, preferably at least 150 mg/day. Preferably the chelating agent is CaEDTA.

Kits

The present invention provides a kit for treating or preventing inflammation in the lung containing (i) an inhalable formulation containing a high concentration of a chelating agent; and (ii) instructions for use.

The present invention provides a kit for treating or preventing inflammation in the lung containing (i) an inhalable formulation capable of delivering a high concentration of an inhalable chelating agent as a single dose; and (ii) instructions for use.

Preferably the high concentration chelating agent is provided in a dosage form containing at least 37.5 mg/dose, at least 50 mg/dose, or between 37.5 mg/dose and 300 mg/dose, or between 50 mg/dose and 300 mg/dose. The chelating agent may be administered between one and four times daily, up to a total dose of up to about 1,200 mg/day, preferably at least 150 mg/day. Preferably the chelating agent is CaEDTA.

In an embodiment, the kit of the present invention comprises a formulation comprising a therapeutically effective amount of a high concentration of an inhaled chelating agent. In an alternative embodiment, the formulation is in premeasured, premixed and/or pre-packaged. Preferably, the inhalation solution is sterile.

The kit of the present invention may also include instructions designed to facilitate user compliance. Instructions, as used herein, refers to any label, insert, etc., and may be positioned on one or more surfaces of the packaging material, or the instructions may be provided on a separate sheet, or any combination thereof. For example, in an embodiment, the kit of the present invention comprises instructions for administering the formulations of the present invention. In one embodiment, the instructions indicate that the formulation of the present invention is suitable for the treatment of lung inflammation. Such instructions may also include instructions on dosage, as well as instructions for administration via nebulizer or dry powder inhaler.

The inhaled chelating agent and any further active agent can be packaged individually so to allow a practitioner or user to formulate each into a pharmaceutical formulation as needed. Alternatively, the pharmaceutical formulation comprising the inhaled chelating agent and any further active agent can be packaged together, thereby requiring de minimus formulation by the practitioner or user. In any event, the packaging should maintain chemical, physical, and aesthetic integrity of the active ingredients.

General

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg. size, displacement and field strength etc.). A range of values will be understood to include all values within the range, including the values defining the range, and values adjacent to the range which lead to the same or substantially the same outcome as the values immediately adjacent to that value which defines the boundary to the range. Accordingly, unless indicated to the contrary, the numerical parameters set forth in the specification and claims are approximations that may vary depending upon the desired properties sought to be obtained by the present invention. Hence "about 80%" means "about 80%" and also "80%". At the very least, each numerical parameter should be construed in light of the number of significant digits and ordinary rounding approaches.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs. The term "active agent" may mean one active agent, or may encompass two or more active agents.

The following examples serve to more fully describe the manner of using the above-described invention, as well as to set forth the best modes contemplated for carrying out various aspects of the invention. It is understood that these methods in no way serve to limit the true scope of this invention, but rather are presented for illustrative purposes.

EXAMPLES

Further features of the present invention are more fully described in the following non-limiting Examples. This description is included solely for the purposes of exemplifying the present invention. It should not be understood as a restriction on the broad description of the invention as set out above.

Example 1: Method of Treating or Preventing Infection in the Lung by Administering a High Concentration of an Inhaled Chelating Agent Biofilms were grown in a realistic in vitro model using suspended drops of cystic fibrosis mucus harvested from epithelial cell lines (Haley et al. *BMC Microbiol* 2012 12:181). Cultures of a *Pseudomonas aeruginosa* clinical strain (MIC tobramycin >256 µg/ml) were grown into late stationary phase in M63 with no carbon source to mimic nutrient limitation.

Drops of mucus (5 µl) were suspended from an inverted IBIDI cover slip and inoculated with $10^3$ colony forming units (CFU), then incubated in a humidified environment at 35° C. for 72 hours to allow biofilm development. Drops were then treated for 5 min with either nebulised tobramycin (20 mg/ml), aerosolised CaEDTA particles (10 mg/ml), or both. Controls were treated with a 50/50 solution of nebulised 0.9% saline/water. Following treatment, the drops were incubated for 16 hours, then stained with BacLight LIVE/DEAD (1 µl), and fixed in paraformaldehyde vapour for 30 min. Biofilms were visualised using confocal microscopy.

Figure 1B:
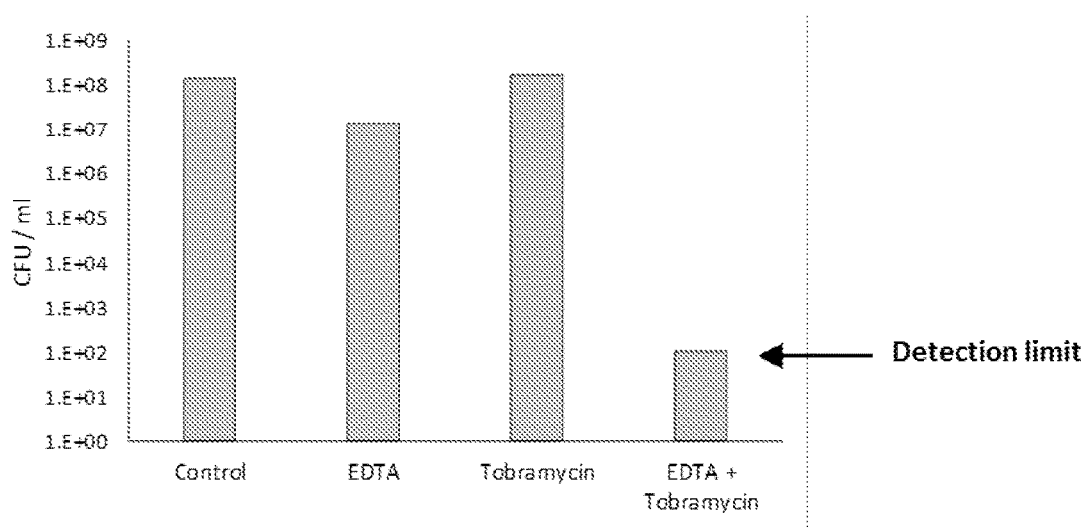

FIG. 1A shows thick and robust biofilms with mostly live cells (green) after treatment with nebulised saline. As expected with a resistant strain, tobramycin treatment alone has little effect on viability. EDTA alone causes some degree of killing (red cells). Strikingly, a combination of tobramycin and EDTA kills the vast majority of biofilm cells. FIG. 1B shows a quantitative representation of the microscopy images in FIG. 1A. Control biofilms were $1\times10^8$ CFU/ml, while EDTA-tobramycin treated biofilms were reduced by >6 orders of magnitude to <$10^2$ CFU/ml.

Patients with CF aged ≥6 years admitted to hospital with an exacerbation were randomised to receive EDTA or saline (placebo) in addition to their usual treatment of intravenous antibiotics and nebulised tobramycin. EDTA was administered together with tobramycin as a nebulised solution of 4 ml 50 mM $CaNa_2EDTA$, 111 mM Tris in 0.9% saline, pH 7.1. Following randomisation, subjects were treated in hospital for two weeks during which they received the treatment four times a day (300 mg EDTA/day, or up to 3.3 mg EDTA/kg/day). Patients were then discharged and treatment was continued twice a day for four weeks. Patients were monitored for a further four weeks, bringing the total study time to 10 weeks.

Sputum was induced with nebulised 3% hypertonic saline at 8-10 L/min for ≥5 minutes. Samples were collected prior to treatment, and at 2, 6 and 10 weeks, processed according to the relevant protocol and stored at −80° C. Mucus was dissected from the clear sputum mixed with Sputalysin (1 ml per gram sputum), vortexed and incubated for an hour, then placed into Skim Milk Glycerol storage medium and stored at −80° C.

Sputum samples were obtained by expectoration from subjects at initial screening, then on Visit 3 (after around 2 weeks), Visit 5 (6 weeks) and finally at follow-up (10 weeks). Mucus was dissected from the clear sputum, treated with Sputalysin (1 ml per gram sputum) and placed into Skim Milk Glycerol storage medium (1 ml/100 mg of mucus), mixed by vortexing and stored at −80° C.

Samples were thawed on ice, serial dilutions were made to a maximum of 10-7 from original concentration, and 20 µL of each dilution placed onto each of three culture plates of McConkey (McC) agar or Blood agar (BA). Plates were incubated at 35° C.

*Pseudomonas* spp. were defined as clear or very pale pink lactose negative colonies on McC agar plates. Rough morphology colonies had a metallic sheen and rough colony edges, smooth morphology colonies were slow growing with regular colony boundaries on McC agar, and mucoid morphology colonies were surrounded by large amounts of alginate, secreted by the bacteria.

The numbers of rough, smooth and mucoid colonies were counted at 24 hours on both McC agar and BA plates, the plates were re-incubated for a further 24 hours, and confirmatory counts of each colony morphology were made. Single colonies of each morphology present in each sample were picked and streaked out on BA plates to obtain pure cultures.

Further identification was by Gram stain to confirm the isolate consisted of Gram-negative, rod shaped cells, and confirmation of an oxidase positive status, by rubbing a tiny part of a colony onto an oxidase test strip. Rapid development of an intense blue colour indicates an oxidative positive isolate.

Figure 2:
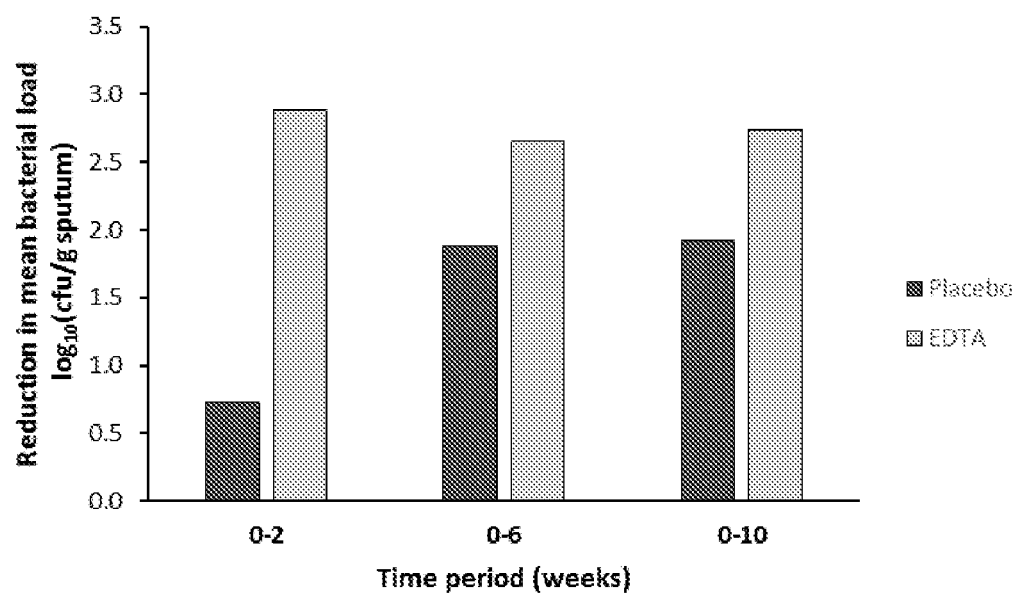
FIG. 2 shows that CaEDTA reduces the bacterial load in CF lungs faster than antibiotic treatment alone. CF subjects were treated with nebulised CaEDTA (EDTA) or saline (placebo), and the bacterial load in expectorated mucus was monitored (colony forming units per gram mucus).

Confirmation of *Pseudomonas* spp. was carried out by testing for resistance to C390 antibiotic. Antibiotic impregnated discs were placed onto a nutrient agar (NA) plate spread with a suspension of the pure isolate in phosphate buffered saline (PBS) to a McFarland density of 0.5. The absence of any zone of inhibition around the disc after overnight incubation at 35° C. indicated resistance to the antibiotic. Single colonies of confirmed *Pseudomonas* spp. (probably *P. aeruginosa*) of each morphological type present in each isolate were picked and resuspended in glycerol/serum storage medium, and stored at −80° C. FIG. 2 shows the change in colony counts for *P. aeruginosa* (McC) at 2 and 6 weeks compared to the start of treatment. After two weeks of treatment, the reduction in colony counts was >400-fold in the EDTA group compared with 4.5-fold in the placebo group.

Example 2: Treatment of Pulmonary Inflammation Results in a Dose-Dependent Increase in FEV1

Subjects with CF ≥6 aged years admitted to hospital with an exacerbation were randomised to receive EDTA or saline (placebo) in addition to their usual treatment of intravenous antibiotics and nebulised tobramycin. EDTA was administered together with tobramycin as a nebulised solution of 4 ml 50 mM CaEDTA, 111 mM Tris in 0.9% saline, pH 7.1. Following randomisation, subjects were treated in hospital for two weeks during which they received the treatment four times a day (300 mg EDTA/day). Following discharge, treatment was continued twice a day for four weeks. Subjects were monitored for a further four weeks, bringing the total study time to 10 weeks.

At each study visit, lung function was measured by spirometry. Data was recorded as the best of three attempts, and results were expressed as % predicted.

Figure 3A:
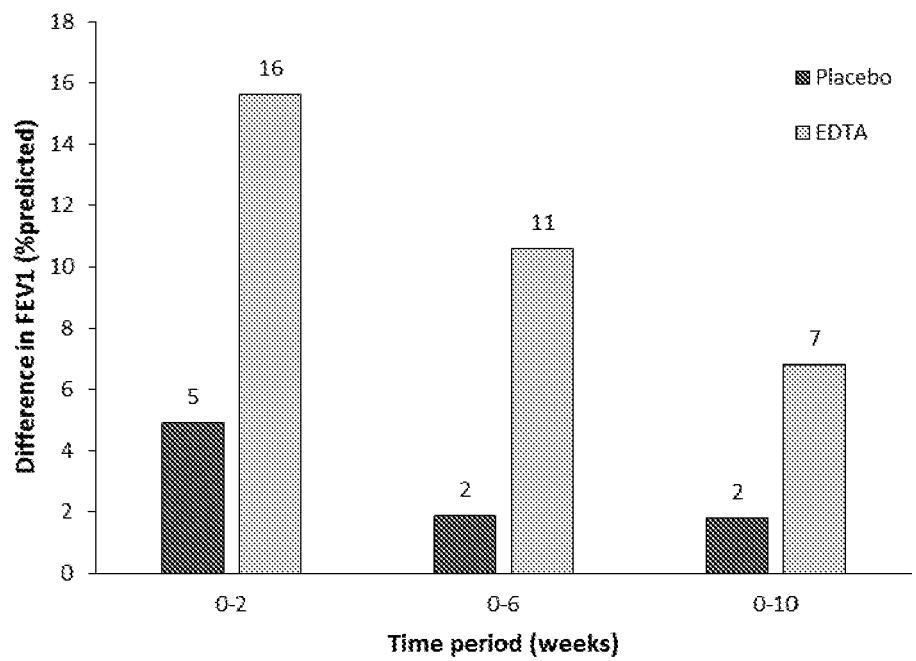
FIG. 3A shows the mean change in FEV1 (% points) in patients treated with CaEDTA or placebo from the start of treatment through to 10 weeks (4 weeks after treatment).
Figure 3B:
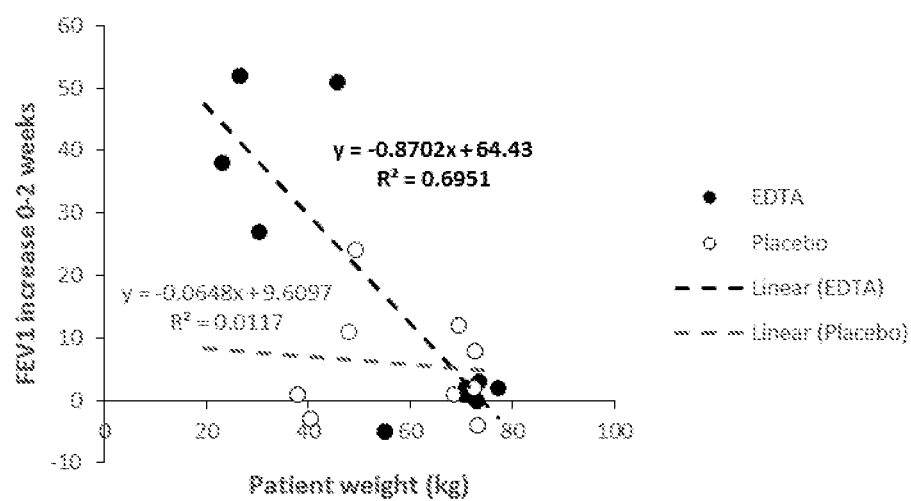
FIG. 3B shows the relationship between FEV1 improvement (0-2 weeks) and body weight.

FIG. 3A shows the mean change in FEV1 for both groups at 2, 6 and 10 weeks after the start of the treatment. The mean increase in FEV1 after 2 weeks was 16% points in the EDTA group vs. 5% points in the placebo group. This difference persisted four weeks after the treatment had been completed with an increase of 7% points in the EDTA group vs 2% point in the placebo group. This demonstrates a clear improvement in lung function in the EDTA group, but little change in the placebo group. FIG. 3B shows an inverse correlation between FEV1 improvement and body weight in the EDTA group ($R2=0.70$), but no correlation in the placebo group treated with tobramycin alone ($R2=0.01$). This shows that EDTA has a dose-dependent effect on lung function (mg EDTA/kg body weight).

Figure 4:
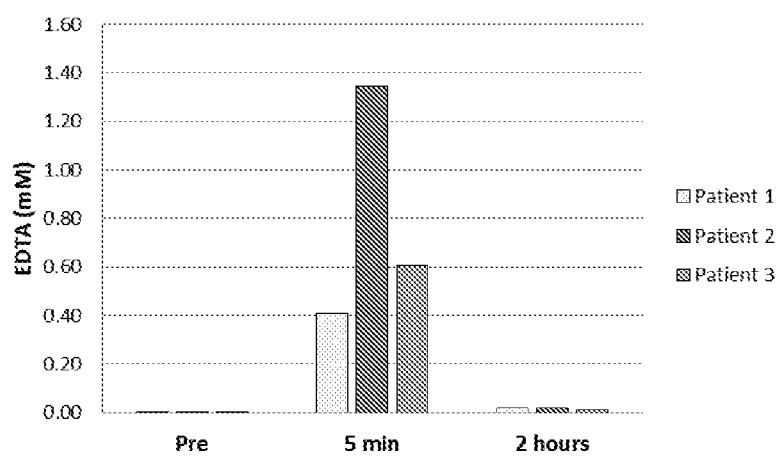
FIG. 4 shows the EDTA concentration achieved in the sputum of three CF subjects 5 minutes and two hours after treatment with 75 mg nebulised CaEDTA.

FIG. 4 shows that delivery of 75 mg CaEDTA to the lungs results in peak concentrations of 0.41-1.34 mM EDTA 5 minutes after the dose.

Example 3: Cigarette Smoke-Induced Pulmonary Inflammation can be Treated by Administering a High Dose of Chelator to the Lungs The effect of a chelator on lung inflammation was tested in a mouse model of chronic obstructive pulmonary disease (COPD). Cigarette smoke (CS) is known to induce pulmonary inflammation, which can be measured by increased leukocyte counts and increased lung weight.

Male BALB/c mice (8 in each group) were exposed to a measured dose of cigarette smoke over a period of two weeks (3 cigarettes, 3 times per day Monday-Friday) or filtered room air. Mice were treated intranasally with the iron chelator deferoxamine (DFO, 3.8 mg in 50 µl) or vehicle three times a day, 30-60 minutes prior to each cigarette smoke exposure for the duration of the experiment. Mice were then terminated, and airways and lungs were assessed for effects on cigarette smoke-induced inflammation and element concentrations.

Bronchoalveolar lavage fluid (BALF) was collected (approximately 1 ml/mouse), and the lungs were surgically removed and weighed. The total number of viable cells in the BALF was determined by mixing equal volumes of trypan blue to BALF and counting manually on a standard Neubauer haemocytometer using a Zeiss Axioscope Fluorescence microscope. Iron was measured by elemental analysis using laser ablation-inductively coupled plasma-mass spectrometry (LA-ICP-MS) and quantified compared to standards of known metal content.

Figure 5:
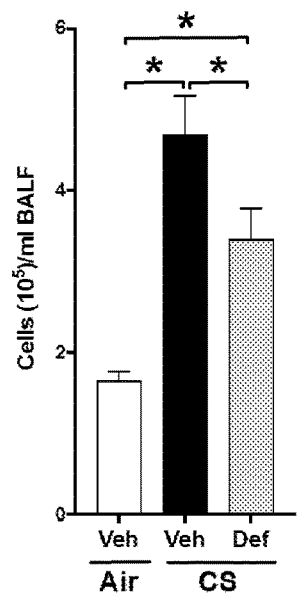
FIGS. 5-7 demonstrate that administration of a high concentration of chelator to mouse lungs reduces inflammation in the absence of infection.

FIG. 5 shows that, as expected, cigarette smoke significantly increases the total number of BALF leukocytes. Treatment with the iron chelator DFO significantly reduces this effect.

Figure 6:
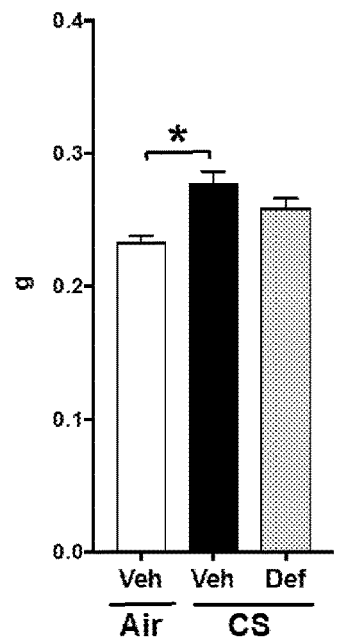

In agreement with this, FIG. 6 shows that average lung weight significantly increases upon treatment with cigarette smoke, but treatment with CFO protects against this effect.

Figure 7:
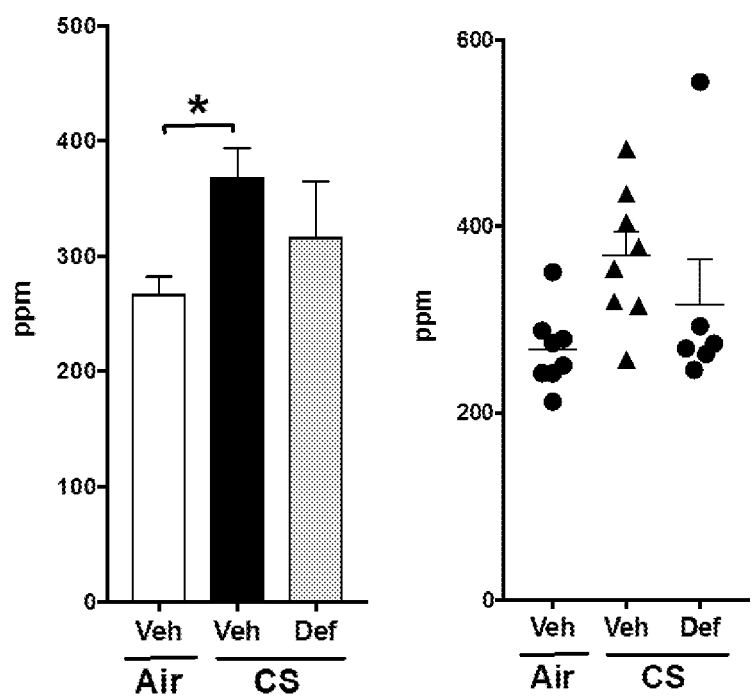

As previously mentioned, Stites et aL (*Am J Respir Crit Care Med.* 1999 160(3):796-80) showed that iron levels are greatly elevated in the lungs of CF patients, as well as in the lungs of smokers, compared to healthy individuals. FIG. 7 (left) confirms that mean iron levels are significantly increased in BALF of mice exposed to cigarette smoke, and that treatment with DFO reduces average BALF iron content. FIG. 7 (right shows that in six of the seven mice treated with DFO (one was lost for reasons unrelated to treatment), BALF iron content was at the same level as that of air-exposed mice.

Prophetic Example P1: In Vivo Study of the Effect of a High Dose of Dry Powder Chelating Agent on Infection, Inflammation, and Oxidative Stress Subjects with CF who need treatment with dry powder tobramycin will be allocated into four cohorts and receive 112 mg dry powder twice a day for 28 days. In addition, Cohort 1 (patients >18 years) will receive ascending doses of dry powder CaEDTA (37.5 mg BID for 1 week; 75 mg BID for 2 weeks, 150 mg BID for 1 week). Cohort 2 (patients >18 years) will receive CaEDTA (37.5 mg BID for 1 week; 75 BID for 2 weeks; 75 mg QID for 1 week). Cohort 3 (patients 12-18 years) will receive CaEDTA (37.5 mg BID for 1 week; 75 mg BID for 2 weeks, 150 mg BID for 1 week. Finally, an observational cohort will receive tobramycin alone for 28 days.

Sputum samples will be collected weekly and assessed for markers of infection and inflammation. Bacteria will be monitored by sputum colony counts. As a measure of structural damage, levels of matrix metalloproteinases (MMPs) and tissue inhibitors of metalloproteinases (TIMPs) are measured using gelatin zymography and immunoassays, respectively, as previously described (Gaggar et al., *Eur Respir J.* 2011 38(3): 721-727; Garratt et al., *Eur Respir J.* 2015 46(2):384-94). The amount of iron in the sputum is quantified by ICP-MS as previously described (Hunter et al., MBio. 2013 4(4):1-8). The amount of iron-binding proteins is assessed using immunoassays. Myeloperoxidase activity are also assayed as a measure of neutrophilic inflammation as previously described (Gaggar et al., *Eur Respir J.* 2011 38(3): 721-727). 3-chlorotyrosine is measured as a biomarker of the potent oxidant hypochlorous acid. Levels are measured using stable isotope dilution gas chromatography with mass spectrometry (Gaggar et al., *Eur Respir J.* 2011 38(3): 721-727). Protein carbonyls are measured as an indicator of reactive oxygen species (ROS) using a commercial immunoassay kit (Gaggar et al., *Eur Respir J.* 2011 38(3): 721-727). Oxidative stress is assessed by measuring glutathione (GSSG and GSH) using immunoassays as previously described (Kettle et al., *Eur Respir J.* 2014 44(1): 122-9). Gene expression of inflammatory and oxidative stress markers (e.g. IL-8, IL-6, TNFa) will also be monitored by Nanostring, and proteins will be measured by ELISA. Oxidative stress can also be measured via metabolites, such as molondialdehyde (colorimetric assay) or 8-isoprostane (ELISA). Iron will be measured by elemental analysis using laser ablation-inductively coupled plasma-mass spectrometry (LA-ICP-MS).

It would be expected that this experiment would show a reduction in inflammatory markers in the EDTA group compared with the placebo group, and a decrease in iron levels. It would be further expected that this experiment would show a change in the balance between MMPs and TIMPs, especially MMP-9 and TIMP-1, which are associated with progression of bronchiectasis.

It would be further expected that the experiment would show a reduction of bacterial load in sputum and an increase in FEV1 in subjects treated with EDTA compared with control patients.

Prophetic Example P2: In Vitro Study of the Effect of High Dose of Chelating Agent on Inflammation, Lung Damage, and Oxidative Stress Lung epithelial cells are grown in tissue culture and inflammation induced by exposure to Fe(II) or excess oxygen. The cells are treated with CaEDTA (0, 1, 5, 10, 25, 50 mM) for 30 min, 1, 3, 24 and 48 hours.

Immunoassays are used to monitor the change in inflammatory markers, such as IL-6, IL-8, TNF-α, neutrophil elastase and others. Oxidative stress and toxicity is measured by assessing reduced glutathione (GSH) levels and apoptosis based on a TUNEL assay, both using commercial assay kits such as ThermoFisher Scientific's Glutathione Fluorescent Detection Kit and BioVision Inc's TUNEL DNA Gragmentation Assay Kit.

It would be expected that this experiment would show a concentration dependent reduction in inflammatory markers in EDTA-treated cells compared with controls; a reduction in GSH indicting a reduction in reactive oxygen species in EDTA-treated cells compared with controls; and reduced apoptosis, as measured by the TUNEL assay, in EDTA-treated cells compared with controls.

Prophetic Example P3: In Vivo Study of the Effect of High Dose of Nebulised Chelating Agent on Inflammation, Lung Damage, and Oxidative Stress Subjects with CF aged ≥6 years admitted to hospital with an exacerbation are randomised to receive nebulised EDTA or saline (placebo) in addition to their usual treatment of intravenous antibiotics and nebulised tobramycin. EDTA is administered together with tobramycin as a nebulised solution of 4 ml 50 mM CaEDTA, 111 mM Tris in 0.9% saline, pH 7.1.

Following randomisation, subjects are treated in hospital for two weeks during which they receive the treatment four times a day (300 mg EDTA/day, or up to 3.3 mg EDTA/kg/day). Subjects are then discharged and treatment continued twice a day for four weeks. Subjects are monitored for a further four weeks, bringing the total study time to 10 weeks. Sputum is collected by induction with nebulised 3% hypertonic saline at 8-10 L/min for ≥5 minutes. Samples is collected prior to treatment, and at 2, 6 and 10 weeks, processed according to the relevant protocol and stored at −80° C.

Inflammatory Marker Expression

Expectorated sputum is stored in RNAlater®, total RNA is extracted using a Qiagen RNEasy® or similar extraction kit, converted into cDNA, and inflammatory markers monitored using qPCR as described by Sivaneson et al. (*Mol Microbiol* 79, 1353-1366) and quantified relative to known housekeeping genes, such as actin and/or GAPDH.

It would be expected that this experiment would show a mean reduction in the gene expression of inflammatory markers in the EDTA group compared with the placebo group.

Cell Damage, Free Iron and Oxidative Stress

Expectorated sputum is frozen directly without processing and assayed for inflammatory markers as above. As a measure of structural damage, levels of matrix metalloproteinases (MMPs) and tissue inhibitors of metalloproteinases (TIMPs) are measured using gelatin zymography and immunoassays, respectively as previously described (Gaggar et al., Eur Respir J. 2011 38(3): 721-727; Garratt et al., Eur Respir J. 2015 46(2):384-94). The amount of iron in the sputum is quantified by ICP-MS as previously described (Hunter et al., MBio. 2013 4(4):1-8). The amount of iron-binding proteins is assessed using immunoassays. Oxidative stress is assessed by measuring glutathione (GSSG and GSH) using immunoassays as previously described (Kettle et al., Eur Respir J. 2014 44(1):122-9).

It would be expected that this experiment would show a reduction in inflammatory markers in the EDTA group compared with the placebo group. It would be further expected that this experiment would show a change in the balance between MMPs and TIMPs, especially MMP-9 and TIMP-1, which are associated with progression of bronchiectasis.

Prophetic Example P4: In Vivo Study of the Effect of a High Dose of Chelating Agent on Inflammation, Lung Damage, and Oxidative Stress A single centre, randomised, double blind, crossover study of cystic fibrosis subjects is carried out. Subjects are randomised for treatment with inhaled CaEDTA or saline (placebo) for two weeks. This is followed by a washout period and then two weeks of the other treatment (EDTA or placebo).

Iron levels, inflammatory markers, MMP/TIMP and FEV1 are monitored as above. Myeloperoxidase activity is also assayed as a measure of neutrophilic inflammation as previously described (Gaggar et al., Eur Respir J. 2011 38(3): 721-727). 3-chlorotyrosine will be measured as a biomarker of the potent oxidant hypochlorous acid. Levels are measured using stable isotope dilution gas chromatography with mass spectrometry (Gaggar et al., Eur Respir J. 2011 38(3): 721-727). Protein carbonyls are measured as an indicator of reactive oxygen species (ROS) using a commercial immunoassay kit (Gaggar et al., Eur Respir J. 2011 38(3): 721-727).

It would be expected that this experiment would show reduced levels of iron and inflammatory markers, an altered MMP/TIMP balance, and increased mean FEV1 in subjects treated with EDTA compared with placebo. It would be further expected that this experiment would show reduced myeloperoxidase activity and lower mean levels of chlorotyrosine and carbonyls.

Clinical data demonstrates efficacy at 300 mg/day for two weeks. The same study demonstrates that 150 mg/day (75 mg BID) is beneficial for lung function and infection (FIG. 2 for reduced bacterial counts; FIG. 3A for improved lung function). Given the significant magnitude of the improvement (FEV1 average 16% points), as would be understood by persons skilled in the art, it is highly likely that much lower doses are effective, i.e. 75 mg/day (37.5 mg BID), as envisaged by Prophetic Example P1.

FIG. 4 shows that a single dose of 75 mg CaEDTA results in up to 1.34 mM EDTA inside mucus plugs after 30 minutes. It is known that penetration of drugs like tobramycin into CF sputum is significantly retarded (Kuhn, R. J. (2001). Formulation of aerosolized therapeutics. Chest 120, 94S-98S), and the concentration of EDTA in the airway surface liquid is therefore most likely substantially higher than that in the centre. It would therefore be reasonable to expect that a daily dose of 37.5 mg (4-fold lower than the lower dose with clinical benefits) would show efficacy in a fully powered study. This would especially be the case in younger patients who receive a higher dose per body weight and generally show a greater response in FEV1 (FIG. 3B).

Numerous variations and modifications of the above-described modes of carrying out the various embodiments of this invention will be apparent to those skilled in the art, based on the above teachings related to the disclosed invention, without departing from the basic inventive concepts. The above embodiments of the invention are merely exemplary and should not be construed to be in any way limiting and all such variations and modifications are to be considered within the scope of the present invention, the nature of which is to be determined from the foregoing description.

Work on this invention was supported by awards from Cystic Fibrosis Foundation Therapeutics.

The invention claimed is:

1. A method of treating inflammation in the lung by administering from 37.5 mg/day to 1,200 mg/day of an inhaled chelating agent wherein the chelating agent is at a concentration of at least 50 mM in one or more doses, and wherein each of the one or more doses of the chelating agent is administered over a period of no more than 2h.

2. The method of claim 1 wherein the chelating agent is CaEDTA.

3. The method of claim 1 wherein the treatment of inflammation results in an increase in FEV.

4. The method of claim 1 wherein the treatment of inflammation is associated with a decrease in MMP activity.

5. The method of claim 1 wherein the treatment of inflammation is associated with a decrease in the production of hydroxyl radicals.

6. The method of claim 1 wherein the chelating agent is combined with tris(hydroxymethyl)aminomethane (TRIS).

* * * * *